(12) United States Patent
Bürgle et al.

(10) Patent No.: US 6,528,619 B1
(45) Date of Patent: Mar. 4, 2003

(54) INHIBITORS FOR UROKINASE RECEPTOR

(75) Inventors: Markus Bürgle; Heinrich Graeff, both of München; Horst Kessler, Schwalbach; Viktor Magdolen, Kirchheim; Bernhard König, Berg; Marcus Koppitz, Berlin; Christoph Riemer, München; Manfred Schmitt, München; Ulrich Weidle, München, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/402,641

(22) PCT Filed: Apr. 14, 1998

(86) PCT No.: PCT/EP98/02178

§ 371 (c)(1),
(2), (4) Date: Jan. 10, 2000

(87) PCT Pub. No.: WO98/46731

PCT Pub. Date: Oct. 22, 1998

(30) Foreign Application Priority Data

Apr. 11, 1997 (EP) .............................. 97106024

(51) Int. Cl.$^7$ ................................. C07K 7/08
(52) U.S. Cl. .................... 530/327; 530/328; 514/14; 514/15
(58) Field of Search ................... 530/327, 328; 514/15, 14

(56) References Cited

FOREIGN PATENT DOCUMENTS

WO       WO 94/22464       10/1994

OTHER PUBLICATIONS

Magdolen et al., Eur. J. Biochem., 237:743–751 (1996).
Danø et al., Proteolysis and Protein Turnover: Proceedings of the 9$^{th}$ ICOP Meeting, Williamsburg, Virginia, USA, Barrett, A.J. and Bond, J., Editor, Portland Press, London, p. 239–245 (1994).
Appella et al., The Journal of Biological Chemistry, 262(10):4437–4440 (Apr. 1987).
Goodson et al., Proc. Natl. Acad. Sci. USA, 91:7129–7133 (Jul. 1994).
Rettenberger et al, Biological Chemistry Hoppe–Seyler, 376:587–594 (Oct. 1995).
Goretzki et al., Fibrinolysis & Proteolysis, 11(1):11–19 (1997).

*Primary Examiner*—Christopher S. F. Low
*Assistant Examiner*—David Lukton
(74) *Attorney, Agent, or Firm*—George W. Johnston; Patricia S. Rocha-Tramaloni; Eileen M. Ebel (57) ABSTRACT

The present invention provides peptides as inhibitors of the binding of urokinase to the urokinase receptor. The peptides have the general structural formula (I):

$$X^1\text{-}[X^2]_n\text{-}X^3\text{-}X^4\text{-}K\text{-}Y\text{-}F\text{-}X^5\text{-}X^6\text{-}I\text{-}X^7\text{-}W\text{-}[X^8]_m \qquad (I)$$

in which $X^1$, $X^2$, $X^3$, $X^4$, $X^5$, $X^6$, $X^7$ and $X^8$ each denote an aminocarboxylic acid, n and m are each independently 0 or 1, K denotes an aminocarboxylic acid with a lysine side chain, Y denotes an aminocarboxylic acid with a tyrosine side chain, F denotes an aminocarboxylic acid with a phenyl-alanine side chain, I denotes an aminocarboxylic acid with an isoleucine side chain, W denotes an aminocarboxylic acid with a tryptophan side chain, and the monomeric building blocks are linked by —CONR$^1$— or —NR$^1$CO— bonds where R$^1$ in each case independently denotes hydrogen, methyl or ethyl, and pharmaceutically compatible salts and derivatives thereof.

16 Claims, 3 Drawing Sheets

INHIBITORS FOR UROKINASE RECEPTOR

FIELD OF THE INVENTION

The present invention concerns peptides as inhibitors of the binding of urokinase to the urokinase receptor. These peptides which are preferably cyclic are suitable as pharmaceutical agents for diseases which are mediated by urokinase and its receptor.

BACKGROUND OF THE INVENTION

The serine protease uPA (urokinase-type plasminogen activator) is responsible for various physiological and pathological processes such as the proteolytic degradation of extracellular matrix material which is necessary for the invasiveness and migration of cells and for tissue remodelling. uPA binds with high affinity ($K_D=10^{-10}$–$10^{-9}$ M) to the membrane-based uPA receptor (uPAR) on the cell surface.

The binding of uPA to its receptor is involved in many invasive biological processes such as the metastatic spread of malignant tumours, trophoplast implantation, inflammation and angiogenesis. Hence antagonists of uPA are able to inhibit the invasiveness, metastatic spread and angiogenesis of tumours. uPA antagonists can be used as agents for the treatment of invasive and metastasising cancer diseases in which uPA and uPAR occur at the invasive foci of tumours (Dano et al., The receptor for urokinase plasminogen activator: Stromal cell involvement in extracellular proteolysis during cancer invasion, in: Proteolysis and Protein Turnover, Barrett, A. J. and Bond, J., Editor, Portland Press, London, 1994, 239) e.g. in cancers of the breast, lung, intestine and ovaries. In addition uPA antagonists can also be used for other purposes in which it is necessary to inhibit the proteolytic activation of plasminogen, for example to treat diseases such as arthritis, inflammation, osteoporosis, retinopathies and for contraception.

The uPA receptor is described in WO 90/12091 and in the publications by Ploug et al., J. Biol. Chem. 268 (1993), 17539 and Ronne et al., J. Immunol. Methods 167 (1994), 91.

uPA is synthesized as a single chain molecule (pro-uPA) and is converted enzymatically into an active two-chain uPA. The uPA molecule is composed of three structurally independent domains, the N-terminal growth factor-like domain (GFD, uPA 1–46), a kringle structure domain (uPA 45–135) and the serine protease domain (uPA 159–411). GFD and the kringle domain together form the so-called aminoterminal fragment of uPA (ATF, uPA 1–135) which is produced by further proteolytic cleavage of two-chain uPA. ATF binds to the uPA receptor with a similar affinity to uPA.

The receptor-binding region of uPA spans the region of the amino acids 12 to 32 since a peptide which contains the amino acid residues 12 to 32 of uPA (in which case cysteine is replaced by alanine in position 19) competes with ATF for binding to the uPA receptor (Appella et al., J. Biol. Chem. 262 (1987), 4437–4440). In this publication it was also shown that this peptide also has an affinity for the uPA receptor after cyclization by bridging the two cysteine residues at positions 12 and 32. In an alternative approach Goodson et al., (Proc. Natl. Acad. USA 91 (1994), 7129–7133) identified antagonistic uPA peptides for the uPAR by screening a bacteriophage peptide library. These peptides had no apparent sequence homology to the natural uPAR-binding sequence of uPA.

Further investigations of the uPAR-binding region of uPA are described in recent publications (Rettenberger et al., Biol. Chem. Hoppe-Seyler 376 (1995), 587–594); Magdolen et al., Eur. J. Biochem. 237 (1996), 743–751; Goretzki et al., Fibrinolysis and Proteolysis 11 (1997), 11–19). The residues Cys19, Lys23, Tyr24, Phe25, Ile28, Trp30 and Cys31 were identified as important determinants for a uPA/uPAR interaction. In these investigations a uPA peptide having the amino acids 16 to 32 of uPA was identified as the most effective inhibitor.

Magdolen et al., (1996) supra analysed the uPAR binding region of the uPA molecule using a peptide having the amino acids 14 to 32 of uPA and peptides derived therefrom. However, these peptides and also peptides used by other research groups (cf. e.g. Appella et al., (1987) supra) have a relatively low affinity for uPAR.

WO-A-94/22464 discloses peptides with a length of 6 to 18 amino acids which are derived from the region of the amino acids 14 to 33 of uPA. It is described that short peptides derived from uPA (uPA 21–29 and uPA 21–26) are able to influence the growth of keratinocytes. Although WO-A-94/22464 makes reference to a potential use of the claimed peptides to block the uPA/uPAR interaction, no data or information whatsoever is shown on such binding studies. Moreover, the peptides uPA 21–29 and uPA 21–26 which are said to be preferred do not contain the minimal uPAR binding region in the uPA molecule which comprises the sequence region of amino acids 19 to 31. Hence the influence of the growth of keratinocytes by these short peptides is very probably not due to a uPA/uPAR interaction.

A disadvantage of the previously known uPA peptide inhibitors is that the affinity of the binding to the uPA receptor is relatively low and inadequate for a therapeutic application. Thus there is a great need for new uPA peptide antagonists which have a higher affinity for the receptor.

SUMMARY OF THE INVENTION

The present invention provides a peptide having the general structural formula (I):

$$X^1\text{-}[X^2]_{n\text{-}x}\text{-}X^3\text{-}X^4\text{-}K\text{-}Y\text{-}F\text{-}X^5\text{-}X^6\text{-}I\text{-}X^7\text{-}W\text{-}[X^8]_m \qquad (I)$$

in which $X_1$, $X^2$, $X^3$, $X^4$, $X^5$, $X^6$, $X^7$ and $X^8$ each denote an aminocarboxylic acid, n and m are each independently 0 or 1, K denotes an aminocarboxylic acid with a lysine side chain, Y denotes an aminocarboxylic acid with a tyrosine side chain, F denotes an aminocarboxylic acid with a phenyl-alanine side chain, I denotes an aminocarboxylic acid with an isoleucine side chain, W denotes an aminocarboxylic acid with a tryptophan side chain, and the monomeric building blocks are linked by —CONR$^1$— or —NR$^1$CO— bonds where R$^1$ in each case independently denotes hydrogen, methyl or ethyl, and pharmaceutically compatible salts and derivatives thereof.

The present invention also provides a pharmaceutical composition comprising at least one peptide of formula I as an active substance.

The present invention further provides the use of a peptide of formula I as a urokinase (uPA) antagonist.

The present invention further provides the treatment of a tumor by the use of a peptide of formula I.

In quantitative investigations it was surprisingly found that the linear peptide uPA (19–31) and cyclic derivatives of this peptide have a considerably improved binding affinity for the uPA receptor.

Experimental data have shown that the peptides according to the invention can be used as uPA antagonists which bind with high affinity to the uPAR. Cyclic peptides are particularly preferred which are characterized by bridges, especially disulfide bridges which do not occur in the native uPA molecule.

Hence the present invention concerns peptides having the general structural formula (I):

$$X^1-[X^2]_n-X^3-X^4-K-Y-F-X^5-X^6-I-X^7-W-[X^8]_m \quad (I)$$

in which
$X^1$, $X^2$, $X^3$, $X^4$, $X^5$, $X^6$, $X^7$ and $X^8$ each denote an amino-carboxylic acid, preferably an a-aminocarboxylic acid,
n and m are each independently 0 or 1,
K denotes an aminocarboxylic acid, preferably an α-aminocarboxylic acid with a lysine side chain,
Y denotes an aminocarboxylic acid, preferably an α-aminocarboxylic acid with a tyrosine side chain,
F denotes an aminocarboxylic acid, preferably an α-aminocarboxylic acid with a phenylalanine side chain,
I denotes an aminocarboxylic acid, preferably an α-aminocarboxylic acid with an isoleucine side chain,
W denotes an aminocarboxylic acid, preferably an α-aminocarboxylic acid with a tryptophan side chain,
and the monomeric building blocks are linked by —CONR¹— or —NR¹CO— bonds in where R¹ in each case independently denotes hydrogen, methyl or ethyl, and pharmaceutically compatible salts and derivatives thereof.

In addition to peptides which contain a sequence having the structural formula (I), pharmaceutically compatible salts and derivatives thereof are also suitable as uPA antagonists. Suitable derivatives are in particular compounds in which the reactive groups of the side chain or/and of the N-terminus or C-terminus e.g. amino or carboxylic acid groups have been modified. Examples of such modifications are acylation e.g. an acetylation of amino groups or/and an amidation or esterification of carboxylic acid groups.

Natural amino acids or enantiomers thereof or non-natural amino acids i.e. amino acids that are not genetically coded such as γ-aminobutyric acid, β-alanine can be used as building blocks for the peptides according to the invention.

The monomeric building blocks are linked by acid amide bonds NR¹CO or CONR¹ i.e. the direction of the peptide sequence can also be reversed (retropeptides). As in native polypeptides, R¹ can denote hydrogen. On the other hand, R¹ can also denote an alkyl residue e.g. methyl or ethyl and in particular methyl since N-alkylation of the amide bond often has a major influence on the activity (cf. e.g. Levian-Teitelbaum et al., Biopolymers 28 (1989), 51–64).

The α-aminocarboxylic acids can also be used as monomeric building blocks in the form of L-enantiomers or/and D-enantiomers. The spatial structure of the peptides according to the invention can be modified by changing the chirality which can also influence the activity. Retro-inverso peptides are particularly preferred i.e. peptides which are present in a reversed sequence direction and contain D-amino acids as monomeric building blocks. In these D-inverso structures the functional side chains have a similar spatial orientation to those in the native peptide sequence, but their biological degradation is impaired due to the presence of D-amino acids and they therefore have advantages as drugs (cf. for example Wermuth et al., J. Am. Chem. Soc. 119 (1997), 1328–1335 and references cited therein).

The peptides according to the invention are preferably cyclic compounds in which in particular the monomeric building blocks $X^1$ and $X^7$ and $X^1$ and $X^8$ are bridged together. This bridge is preferably not a natural bridge i.e. a bridge which does not occur in natural uPA. It can for example utilize the side chains of the respective α-aminocarboxylic acid residues in which case bridging by means of disulfide bonds e.g. between two cysteine residues (corresponding to a bridge between Cys¹⁹ and Cys³¹ of the natural uPA sequence) is particularly preferred. Other types of cyclization between amino acid side chains are, however, also possible e.g. amide bonds between an amino acid with an ω amino side group e.g. Lys and an amino acid with a carboxylic acid side group such as Asp or Glu. In addition the disulfide bridge can also be replaced by an alkylene bridge in order to increase the chemical stability. In addition an amino acid side chain may also be linked to the peptide backbone e.g. an omega amino side group may be linked with the C-terminal end or a carboxylic acid side group may be linked with the N-terminal end. A linkage of the N-terminus and C-terminus is also possible.

Instead of the disulfide bridge it is also possible to use so-called turn mimetics (Haubner et al., J. Am. Chem. Soc. 118 (1996), 7884–7891) or sugar amino acids (Graf von Rbdern et al., J. Am. Chem. Soc. 118 (1996), 10156–10167).

In a particularly preferred embodiment of the present invention the peptides have the general structural formula (II):

$$X^1-X^2-X^3-X^4-K-Y-F-X^5-X^6-I-X^7-W-X^8 \quad (II)$$

in which $X^1$, $X^2$, $X^3$, $X^4$, $X^5$, $X^6$, $X^7$, $X^8$, K, Y, F, I and W are defined as above and $X^1$ and $X^8$ are bridged together.

In yet a further preferred embodiment the peptides according to the invention have the general structural formula (III):

$$X^1-X^3-X^4-K-Y-F-X^5-X^6-I-X^7-W \quad (III)$$

in which $X^1$, $X^3$, $X^4$, $X^5$, $X^6$, $X^7$, K, Y, F, I and W are defined as above and $X^1$ and $X^7$ are bridged together.

The monomeric building blocks $X^1$ to $X^8$ preferably have the following meanings:
$X^1$ and—if present—$X^8$ are α-aminocarboxylic acid building blocks with an SH side chain, in particular with a cysteine side chain.
$X^2$—if present—is preferably an α-aminocarboxylic acid with an aliphatic and uncharged side chain e.g. valine, leucine or isoleucine, in particular valine.
$X^3$—if present—and $X^5$ are α-aminocarboxylic acids with an aliphatic hydrophilic side chain such as serine or threonine, in particular serine.
$X^4$ and $X^6$ are preferably α-aminocarboxylic acids with an aliphatic hydrophilic side chain, in particular an amide side chain such as asparagine or glutamine, in particular asparagine.

In compounds having the structural formula (II) $X^7$ is preferably a basic α-aminocarboxylic acid, in particular histidine. In compounds of the structural formula (III) $X^7$ is an α-aminocarboxylic acid with an SH side group, in particular cysteine.

The present invention additionally concerns a pharmaceutical composition which contains at least one peptide as defined above as the active substance optionally together with common pharmaceutical carriers, auxiliary agents or diluents. The peptides according to the invention are used especially to produce uPA antagonists which are suitable for treating tumours.

The pharmaceutical compositions according to the invention can be present in any form, for example as tablets, as coated tablets or in the form of solutions or suspensions in aqueous or non-aqueous solvents. The peptides are preferably administered orally or parenterally in a liquid or solid form. When they are administered in a liquid form, water is preferably used as the carrier medium which optionally contains stabilizers, solubilizers or/and buffers that are usually used for injection solutions. Such additives are for example tartrate or borate buffer, ethanol, dimethyl sulfoxide, complexing agents such as EDTA, polymers such as liquid polyethylene oxide etc.

If they are administered in a solid form, then solid carrier substances can be used such as starch, lactose, mannitol, methyl cellulose, talcum, highly dispersed silicon dioxide, high molecular fatty acids such as stearic acid, gelatin, agar, calcium phosphate, magnesium stearate, animal and vegetable fats or solid high molecular polymers such as polyethylene glycols. The formulations can also contain flavourings and sweeteners if desired for oral administration.

The administered dose depends on the age, state of health and weight of the patient, on the type and severity of the disease, on the type of treatment, the frequency of the administration and the type of desired effect. The daily dose of the active compound is usually 0.1 to 50 mg/kilogramme body weight. Normally 0.5 to 40 and preferably 1.0 to 20 mg/kg/day in one or several doses are adequate to achieve the desired effects.

BRIEF DESCRIPTION OF THE DRAWINGS

The invention is further illustrated by the examples described in the following and the figures.

EXAMPLES

1. Methods
1.1 Solid Phase Peptide Synthesis

Linear peptides were synthesized on a 2-chlorotrityl resin (Barlos et al., Int. J. Pept. Protein Res. 37 (1991), 513 to 520) using an Applied Biosystems Model 431 A peptide synthesizer or a multiple peptide synthesizer model Syro II (MultiSynTech). Using the orthogonal Fmoc strategy (Carpino and Han, J. Org. Chem. 37 (1972), 3404–3409; Fields and Noble, Int. J. Peptide Protein Res. 35 (1990), 161–214) the amino acid side chains were blocked with the protecting groups trityl (Asn, Cys, Gln and His), tert.-butyloxycarbonyl (Lys and Trp), tert.-butyl (Asp, Glu, Ser, Thr and Tyr), acetamidomethyl (cys) and 2,2,5,7,8-pentamethylchroman-6-sulfonyl or 2,2,4,6,7-pentamethyldihydrobenzofuran-5-sulfonyl (Arg). The coupling was carried out at room temperature in dimethylformamide using a three-fold excess of 2-(lH-benzotriazol-1-yl)-1,1,3,3-tetramethyl-uroniumtetrafluoroborate/1-hydroxybenzotriazole/Fmoc amino acid with 2.5 equivalents of N-ethyldiisopropylamine in N-methyl-pyrrblidone. The Fmoc group was removed by sequential treatment of the resins with an excess of 40% or 20% piperidine in dimethylformamide. The cleavage of the peptides and removal of the side chain protecting groups was carried out simultaneously by treatment with 82.5% trifluoroacetic acid/5% phenol/2.5% ethane dithiol/5% thioanisol/ 5% H$_2$O (0° C./1 h; room temperature/1 h). In the case of Arg groups protected with 2,2,5,5,7,8-pentamethylchroman-6-sulfonyl, the peptides were incubated for an additional 12 h at room temperature. The crude peptides were precipitated at −30° C. with diethyl ether, dissolved in methanol, precipitated as previously described, dissolved in tert.-butanol and lyophilized. Peptides containing tryptophan were additionally treated for 2 h with 5% acetic acid before the lyophilization.

The peptides were purified by HPLC using a reversed phase C18 column (Nucleosil 1005-C18) or a YMC pack ODS column. They were cyclized by forming a disulfide bridge between the cysteine residues. The oxidation required for this was carried out by taking 0.1 to 0.3 mg/ml of the purified linear peptides up in 80% water and 20% DMSO (vol/vol) and removing the solvent under reduced pressure after 10 h. The cyclic peptides were again purified by HPLC as described above.

1.2 Mass Spectroscopy and Amino Acid Analysis

The purified and desalted peptides were analysed on a HPLC system 140 B (Applied Biosystems, Foster City, USA). The UV absorbance was measured with a UVIS 200 detector (Linear Instruments, Reno, USA) at 206 nm. The chromatography was carried out on an Aquapore 3 μ (Applied Biosystems, Foster City, USA) reversed phase column (1 mm×50 mm) at a flow rate of 20 μl/min. The solvent system was 0.1% TFA in water (A) and 0.1% TFA in acetonitrile (B). The HPLC system was coupled to an atmospheric pressure ionisation source which was connected to a tandem quadrupole instrument API III (Sciex, Perkin Elmer, Thornhill, Canada).

The quadrupole M/Z scale was calibrated with the ammonium addition products of polypropylene glycol. The average mass values were calculated from the M/Z peaks in the charge distribution profiles of the multiple charged ions (Covey et al., Rapid Commun. Mass Spectrom. 2 (1988), 249–256; Fenn et al., Science 246 (1989), 64–71).

The amino acid analysis was carried out according to the ninhydrin method using the analytical system 6300 (Beckman Instruments, Fullerton, USA) after hydrolysing the peptides by the TFA-HCl vapour phase method which allows a quantitative determination of the peptide concentration (Tsugita et al., J. Biochem. 102 (1987), 1593–1597).

1.3 Flow Cytometry

The ability of the synthetic peptides to inhibit the uPA/-uPAR interaction was determined by means of flow cytometry on a FACScan flow cytometer (Becton-Dickinson, Heidelberg, Germany) using the human promyeloid cell line U937 as a source of cellular native uPAR (Chuchulowski et al., Fibrinolysis 6, Suppl. 4 (1992), 95–102; Magdolen et al., (1996), supra). The U937 cells were stimulated with 1 mM phorbol-12-myristate-13-acetate (PMA) for 48 h. After stimulation with PMA the U937 cells expressed considerable amounts of cell surface-associated uPAR.

The stimulated cells were treated for 1 min at room temperature with 50 mM glycine HCl, 0.1 NaCl, pH 3.6 in order to dissociate endogenous receptor-bound uPA. Subsequently the acidic buffer was neutralized with 0.5 M HEPES-100 mM NaCl, pH 7.5. The cells were then immediately washed twice with PBS/0.1% bovine serum albumin (BSA) and centrifuged for 10 min at room temperature and 300×g. The cells were resuspended in PBS/0.1% BSA, adjusted to a concentration of $10^6$ cells per ml and simultaneously incubated for 45 minutes at room temperature with 16 ng FITC-conjugated pro-uPA and various amounts of the synthetic peptides. Before the analysis, propidium iodide, a fluorescent dye which specifically binds double-stranded DNA, was added to each sample in order to determine the viability of the analysed U937 cells. Damaged, propidium iodide-labelled cells were excluded from the analysis.

1.4 Solid Phase uPAR/uPA Binding Test

In addition to the flow cytometric analyses, a solid phase ATF-ligand binding test was carried out in order to examine the interactions of synthetic peptides with the uPAR. For this microtitre plates were coated with recombinant human uPAR from CHO cells (Wilhelm et al., FEBS Lett. 337 (1994), 131–134; Magdolen et al., Electrophoresis 16 (1995), 813–816) and the remaining protein-binding sites were saturated with 2% BSA (weight/vol.). After incubation with the samples (0.6 ng ATF together with 15 µg synthetic peptide per ml) and several wash steps, the amount of ATF which had bound to the immobilized uPAR on the microtitre plate was determined using a biotinylated monoclonal mouse antibody against the kringle domain of ATF (No. 377, American Diagnostics, Greenwich, Conn., USA) and subsequent addition of avidin-peroxidase conjugate and 3,3',5,5'-tetramethylbenzidine/$H_2O$ as a substrate for the peroxidase. The presence of synthetic peptides which compete with the ATF binding to uPAR reduces the conversion of the chromogenis substrate.

2. Results 2.1 Determination of the uPAR Binding Capacity of Synthetic Peptides by Quantitative Flow Cytometric Analysis A comparison was made of the inhibitory capacity of the peptides $uPA_{12-32}$ [C19A] (Appella et al., (1987), supra) the so-called clone 20-peptide AEPMPHSLNFSQYLWYT [SEQ ID NO:10] (Goodson et al., (1994), supra) which was identified as the most effective peptide from a phage peptide library and of the synthetic peptide $uPA_{16-32}$ derived from the wild-type uPA sequence.

Figure 1A:
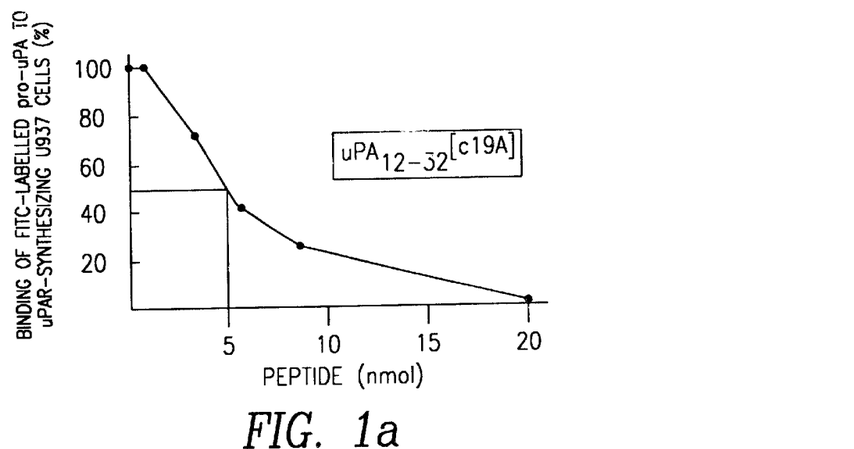
FIG. 1 shows the quantity-dependent inhibition of the binding of pro-uPA to a cell surface-associated uPAR by synthetic peptides.
Figure 1B:
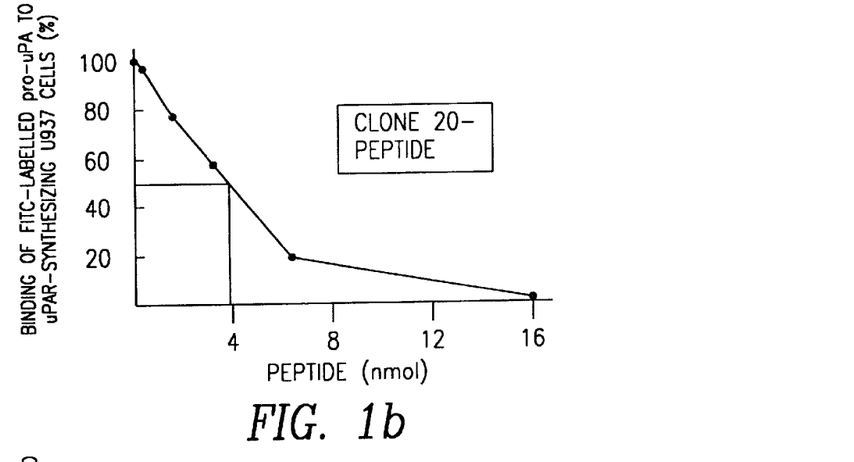
Figure 1C:
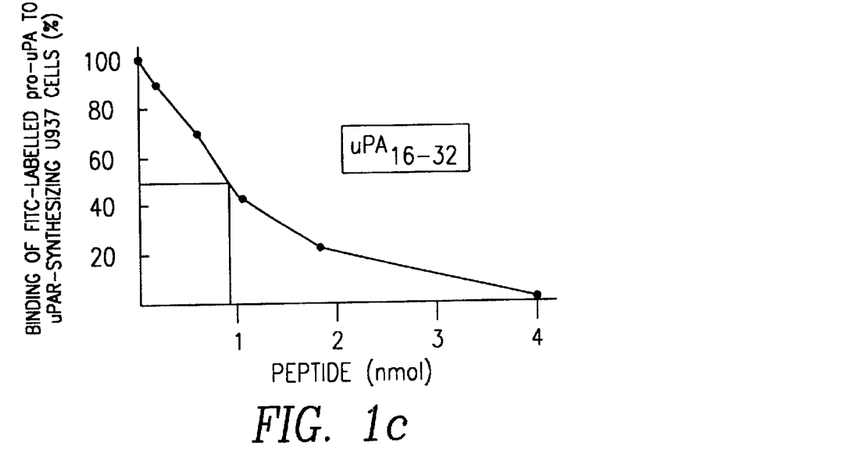

For this the purified peptides were analysed by mass spectroscopy, quantified by amino acid analysis and then tested by flow cytometry according to the method described in 1.3 for their ability to inhibit the binding of fluorescent-labelled pro-uPA to the uPA receptor on U937 cells. It was found that pro-uPA is displaced in a dose-dependent manner from the cell surface-associated uPAR by all three synthetic peptides (FIG. 1). An approximately 15,000 to 12,000 molar excess of $uPA_{12-32}$ [C19A] or clone 20 peptide resulted in a 50% inhibition of the binding of uPA. The peptide $uPA_{16-32}$ exhibited a 4- to 5-fold higher affinity to uPAR compared to the two other peptides: an approximately 3,000-fold molar excess is sufficient to achieve a 50% inhibition.

Furthermore it was found that the linear peptide $uPA1_{9-31}$ [SEQ ID NO:1] surprisingly has an IC50 value of ca. 0.8 µM whereas the IC50 value for $uPA_{16-32}$ is ca. 3.2 µM.

2.2 Determination of the uPAR Binding Capacity of Synthetic Peptides in a Microtitre Plate Solid Phase Ligand Binding Test A series of peptides with variable sequence regions from the receptor binding region of uPA were synthesized and were increasingly shortened at the amino terminus starting with $uPA_{10-32}$. The microtitre plate solid phase binding test described in 1.4 was used to determine the inhibitory capacity of these peptides. The results of this test are shown in FIG. 2.

Figure 2A:
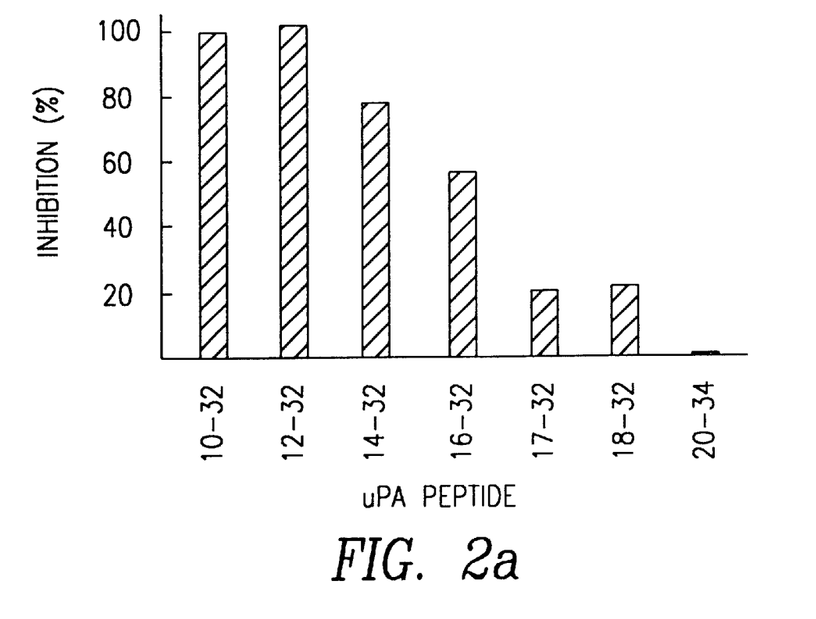
FIG. 2 shows the competition of synthetic peptides with ATF for binding to the uPAR.
Figure 2B:
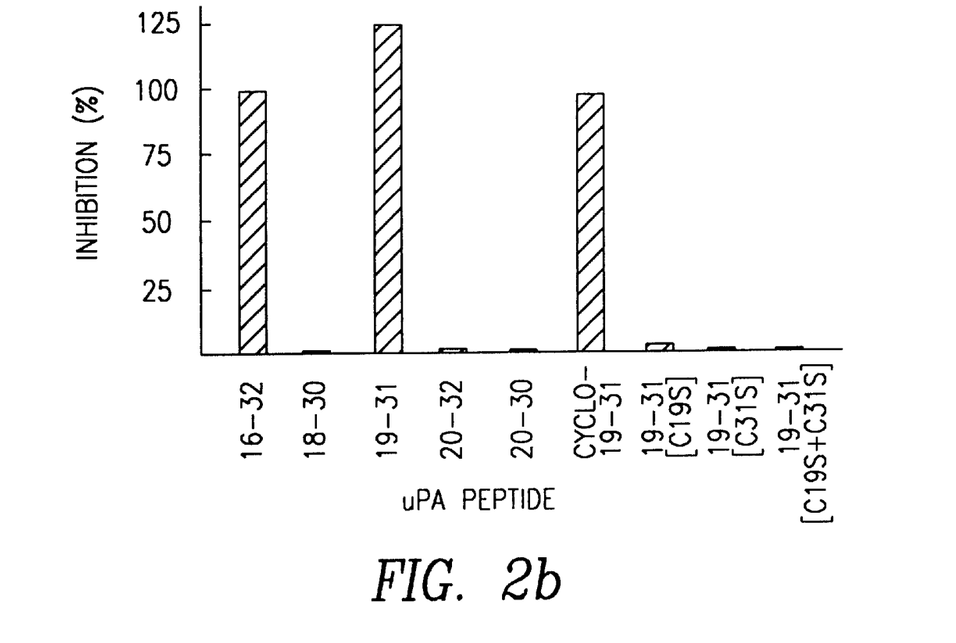

It can be seen in FIG. 2A that the peptides $uPA_{10-32}$, $uPA_{12-31}$, $uPA_{14-32}$ and $uPA_{16-32}$ effectively inhibit the binding of ATF to uPAR. The peptides $uPA_{17-32}$ and $uPA_{18-34}$ have considerably reduced uPAR binding capacities. The peptide $uPA_{20-34}$ does not bind at all to the uPAR. In a further experiment the binding capacity of the peptlde's $uPA_{19-31}$ [SEQ ID NO: 1], $uPA_{18-30}$, $uPA_{20-32}$ and $uPA_{20-30}$ was tested. The result of this experiment is shown in FIG. 2B. Surprisingly it was found that $uPA_{9-31}$ binds to the uPAR with higher affinity than the longer peptide $uPA_{16-32}$. The other tested linear peptides had no significant binding capacity.

The cyclic peptide $cyclo^{19,31}uPA_{19-31}$ [SEQ ID NO: 1] which contains an intramolecular disulfide bond between the cysteine residues at positions 19 and 31 was surprisingly still able to inhibit the binding of uPA to the uPA receptor. Furthermore the binding activity of $cyclo^{19,31}uPA19-31$ [SEQ ID NO:1] was significantly more stable after long storage in aqueous solution or repeated freeze/thaw cycles than the linear peptlde $uPA_{19-31}$ [SEQ ID NO:1].

2.3 Synthesis of Modified Cyclic uPA Peptides

A series of additional cyclic peptides were prepared using $cyclo^{19,31}uPA_{19-31}$ [SEQ ID NO: 1] as the lead structure in which certain amino acids were deleted and/or substituted by other amino acids. The structures of the new synthesized peptide variants are shown in FIG. 3 [SEQ ID NOs:2, 3, 4, 5, 6, 7, 8, and 9].

SEQUENCE LISTING

<160> NUMBER OF SEQ ID NOS: 10

Figure 3A:
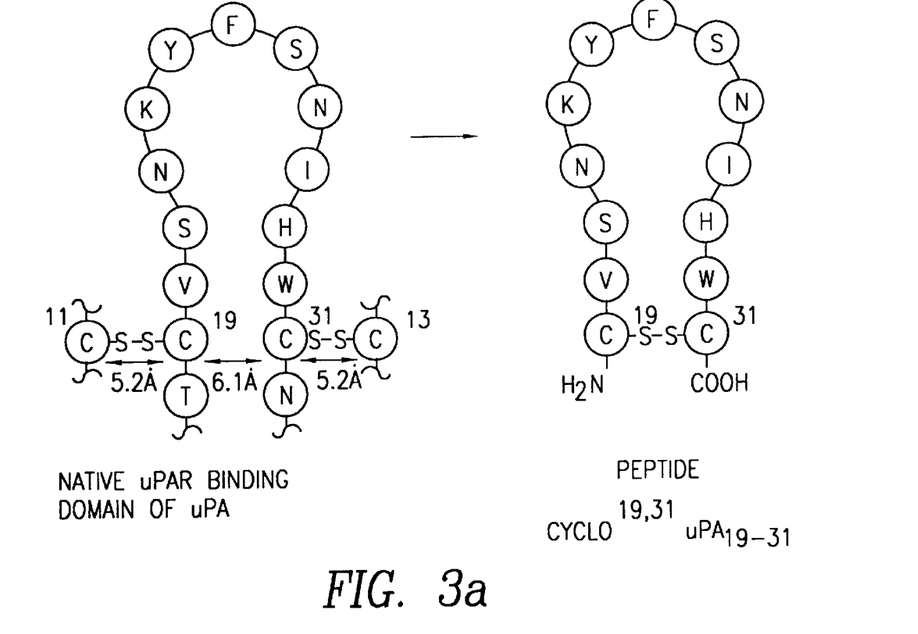
FIG. 3A shows the structure of cyclo$^{19-31}$ uPA 19–31 (SEQ ID NO:1) (right) compared to the structure of the corresponding domain from native uPA
Figure 3B:
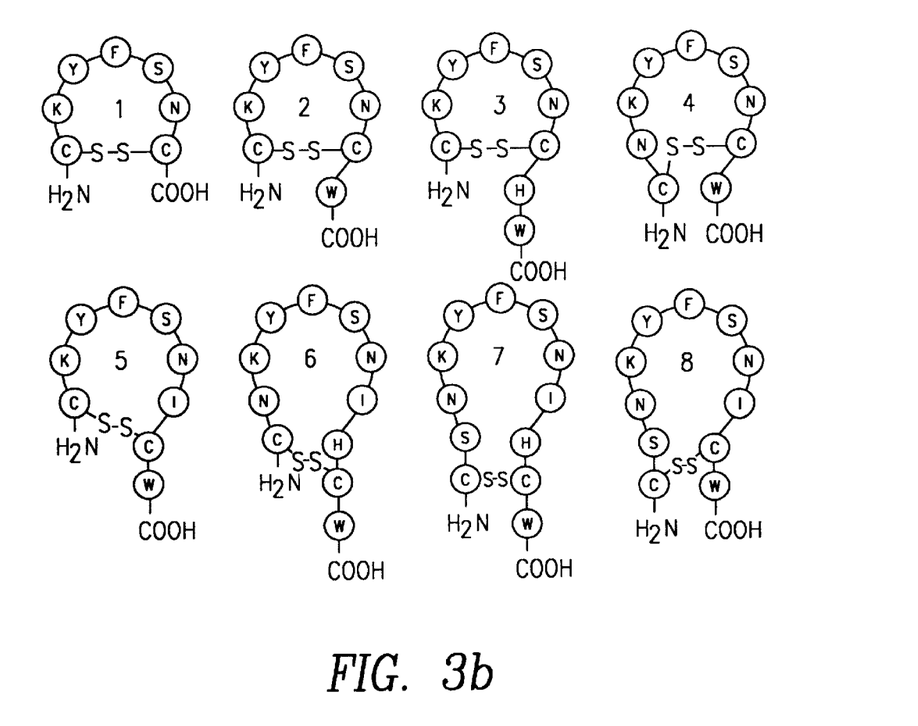
FIG. 3B shows the structure of various cyclic peptide derivatives of cycr6$^{19,31}$ uPA 19–31(SEQ ID NOs: 1, 2, 3, 4, 5, 6, 7, 8, and 9.

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:Peptide
      "cyclo 19,31 uPA 19-31"; Figure 3A

<400> SEQUENCE: 1

Cys Val Ser Asn Lys Tyr Phe Ser Asn Ile His Trp Cys

```
                1               5                  10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:Peptide 1,
      figure 3B

<400> SEQUENCE: 2

Cys Lys Tyr Phe Ser Asn Cys
  1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:Peptide 2,
      figure 3B

<400> SEQUENCE: 3

Cys Lys Tyr Phe Ser Asn Cys Trp
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:Peptide 3,
      figure 3B

<400> SEQUENCE: 4

Cys Lys Tyr Phe Ser Asn Cys His Trp
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:Peptide 4,
      figure 3B

<400> SEQUENCE: 5

Cys Asn Lys Tyr Phe Ser Asn Cys Trp
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:Peptide 5,
      figure 3B

<400> SEQUENCE: 6

Cys Lys Tyr Phe Ser Asn Ile Cys Trp
  1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:Peptide 6,
``` figure 3B

<400> SEQUENCE: 7

Cys Asn Lys Tyr Phe Ser Asn Ile His Cys Trp
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:Peptide 7,
      figure 3B

<400> SEQUENCE: 8

Cys Ser Asn Lys Tyr Phe Ser Asn Ile His Cys Trp
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:Peptide 8,
      figure 3B

<400> SEQUENCE: 9

Cys Ser Asn Lys Tyr Phe Ser Asn Ile Cys Trp
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence:clone-20
      peptide

<400> SEQUENCE: 10

Ala Glu Pro Met Pro His Ser Leu Asn Phe Ser Gln Tyr Leu Trp Tyr Thr
1               5                   10                  15

What is claimed is:

1. A urokinase receptor antagonist selected from the group consisting of formula (I):

$$X^1\text{-}[X^2]_n\text{-}X^3\text{-}X^4\text{-}K\text{-}Y\text{-}F\text{-}X^5\text{-}X^6\text{-}I\text{-}X^7\text{-}W\text{-}[X^8]_m \quad (I)$$

in which $X^1$, $X^2$, $X^3$, $X^4$, $X^5$, $X^6$, $X^7$, and $X^8$ each denote an aminocarboxylic acid, optionally substituted by an aminocarboxylic acid side chain, wherein the side chain of $X^1$ bears a sulfhydryl group,
the side chain of $X^2$ bears an aliphatic moiety,
the side chain of $X^3$ bears an aliphatic and hydrophilic moiety,
the side chain of $X^4$ bears an aliphatic and hydrophilic moiety,
the side chain of $X^5$ bears an aliphatic and hydrophilic moiety,
the side chain Of $X^6$ bears an aliphatic and hydrophilic moiety,
the side chain of $X^7$ bears a basic moiety or a sulfhydryl group, and
the side chain of $X^8$ bears a sulfhydryl group,
n and m are each independently 0 or 1, K denotes an aminocarboxylic acid with a lysine side chain,
Y denotes an aminocarboxylic acid with a tyrosine side chain,
F denotes an aminocarboxylic acid with a phenylalanine side chain,
I denotes an aminocarboxylic acid with an isoleucine side chain,
W denotes an aminocarboxylic acid with a tryptophan side chain, and the aminocarboxylic acids are linked by —CONR$^1$— or —NR$^1$CO— bonds where R$^1$ in each case independently denotes hydrogen, methyl, or ethyl,
structural formula I wherein amino acid residues $X^1$ and $X^8$ are bridged together, structural formula I wherein amino acid residues $X^1$ and $X^7$ are bridged together, structural formula I wherein amino acid residues $X^1$ and $X^8$ are bridged together by one of their side chains, structural formula I wherein amino acid residues $X^1$ and $X^8$ are bridged together by both of their side chains, structural formula I wherein amino acid residues $X^1$ and $X^7$ are bridged together by one of their side chains, structural formula I wherein amino acid residues $X^1$ and $X^7$ are bridged together by both of their side chains, and pharmaceutically acceptable salts thereof.

2. The urokinase receptor antagonist as claimed in claim 1, wherein $X^1$ denotes an α-aminocarboxylic acid with a cysteine side chain.

3. The urokinase receptor antagonist as claimed in claim 1, wherein $X^2$ denotes an α-aminocarboxylic acid with a valine side chain.

4. The urokinase receptor antagonist as claimed in claim 1, wherein $X^3$ denotes an α-aminocarboxylic acid with a serine side chain.

5. The urokinase receptor antagonist as claimed in claim 1, wherein $X^4$ denotes an α-aminocarboxylic acid with an asparagine side chain.

6. The urokinase receptor antagonist as claimed in claim 1, wherein $X^5$ denotes an α-aminocarboxylic acid with a serine side chain.

7. The urokinase receptor antagonist as claimed in claim 1, wherein $X^6$ denotes an α-aminocarboxylic acid with an asparagine side chain.

8. The urokinase receptor antagonist as claimed in claim 1, wherein $X^7$ denotes an α-aminocarboxylic acid with a histidine or cysteine side chain.

9. The urokinase receptor antagonist as claimed in claim 1, wherein $X^8$ denotes an α-aminocarboxylic acid with a cysteine side chain.

10. The compound as claimed in claim 1 of formula (II):

$$X^1\text{-}X^2\text{-}X^3\text{-}X^4\text{-}K\text{-}Y\text{-}F\text{-}X^5\text{-}X^6\text{-}I\text{-}X^7\text{-}W\text{-}X^8 \qquad (II)$$

in which $X^1$ and $X^8$ are bridged together.

11. The compound as claimed in claim 1 of formula (III):

$$X^1\text{-}X^3\text{-}X^4\text{-}K\text{-}Y\text{-}F\text{-}X^5\text{-}X^6\text{-}I\text{-}X^7\text{-}W \qquad (III)$$

in which $X^1$ and $X^7$ are bridged together.

12. The urokinase receptor antagonist of claim 1, wherein amino acid residues $X^1$ and $X^7$ are bridged together by a disulfide bond.

13. The urokinase receptor antagonist of claim 1, wherein amino acid residues $X^1$ and $X^8$ are bridged together by a disulfide bond.

14. The urokinase receptor-antagonist as claimed in claim 1, consisting of the amino acid sequence of SEQ ID NO:1.

15. A composition comprising a compound of claim 1 in an amount effective to antagonize the urokinase receptor, and a suitable carrier.

16. The composition of claim 15 wherein the carrier is aqueous.

* * * * *

UNITED STATES PATENT AND TRADEMARK OFFICE
CERTIFICATE OF CORRECTION

PATENT NO. : 6,528,619 B1
DATED : March 4, 2003
INVENTOR(S) : Markus Bürgle et al.

It is certified that error appears in the above-identified patent and that said Letters Patent is hereby corrected as shown below:

Title page,
Item [75], Inventors, should read as -- Markus Bürgle, Heinrich Graeff, both of München; Horst Kessler, Schwalbach; Viktor Magdolen, Kirchheim; Bernhard König, Berg; Marcus Koppitz, Berlin; Christoph Riemer, München; Manfred Schmitt, München; Ulrich Weidle, München; Olaf G. Wilhelm, München, all of (DE) --.

Column 13,
Line 3, "cc-aminocarboxylic acid" should read -- α-aminocarboxylic acid --.

Signed and Sealed this

Second Day of September, 2003

JAMES E. ROGAN
*Director of the United States Patent and Trademark Office*